(12) United States Patent
Dunn (10) Patent No.: US 8,052,700 B2
(45) Date of Patent: Nov. 8, 2011

(54) TISSUE CLAMP

(75) Inventor: Raymond M. Dunn, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 164 days.

(21) Appl. No.: 12/070,356

(22) Filed: Feb. 15, 2008

(65) Prior Publication Data

US 2008/0249547 A1    Oct. 9, 2008

Related U.S. Application Data

(63) Continuation-in-part of application No. 11/592,019, filed on Nov. 2, 2006, now Pat. No. 7,901,420.

(60) Provisional application No. 60/732,748, filed on Nov. 2, 2005.

(51) Int. Cl.
*A61B 17/08* (2006.01)

(52) U.S. Cl. ........................................... 606/157

(58) Field of Classification Search .......... 606/151–153, 606/157–158, 210–211, 120; 128/346; 81/177.7–177.8
See application file for complete search history.

(56) References Cited

U.S. PATENT DOCUMENTS

| | | | |
|---|---|---|---|
| 3,579,751 A | 5/1971 | Jonckheere |
| 3,856,016 A | 12/1974 | Davis |
| 4,024,868 A | 5/1977 | Williams |
| 4,433,689 A | 2/1984 | von Zeppelin |
| 4,434,795 A | 3/1984 | Mericle |
| 4,444,187 A | 4/1984 | Perlin |
| 4,476,865 A | 10/1984 | Faila et al. |
| 4,616,651 A | 10/1986 | Golden |
| 4,671,281 A | 6/1987 | Beroff et al. |
| 4,777,950 A | 10/1988 | Kees, Jr. |
| 4,815,466 A | 3/1989 | Perlin |
| 4,834,096 A | 5/1989 | Oh et al. |
| 5,053,045 A | 10/1991 | Schmidt et al. |
| 5,062,846 A | 11/1991 | Oh et al. |
| 5,074,870 A | 12/1991 | von Zeppelin |
| 5,282,812 A | 2/1994 | Suarez, Jr. |
| 5,441,509 A | 8/1995 | Vidal et al. |
| 5,733,295 A | 3/1998 | Back et al. |
| 5,843,101 A | 12/1998 | Fry |
| 5,984,934 A | 11/1999 | Ashby et al. |
| 6,193,732 B1 | 2/2001 | Frantzen et al. |
| 6,226,843 B1 | 5/2001 | Crainich |
| 6,464,710 B1 | 10/2002 | Foster |
| 6,537,289 B1 | 3/2003 | Kayan et al. |
| 6,746,461 B2 | 6/2004 | Fry |
| 7,338,503 B2 | 3/2008 | Rosenberg et al. |
| 2004/0254596 A1 | 12/2004 | Kuester, III |
| 2007/0106314 A1 | 5/2007 | Dunn |

OTHER PUBLICATIONS

Micro Clips, one web page with product information shown, Company—Harvard Apparatus, Holliston, MA, USA, 2009. Clips and Clamps, 10 web pages of product information shown, Company—Roboz Surgical Company, Inc., Gaithersburg, MD, 2009.

*Primary Examiner* — Melanie Tyson
*Assistant Examiner* — Son Dang
(74) *Attorney, Agent, or Firm* — Weingarten, Schurgin Gagnebin & Lebovici LLP (57) ABSTRACT

The present invention relates to a tissue clamp, a tool for grasping the clamp and a method of using the clamp for surgical procedures. The clamp has a fixture or fixtures positioned on the proximal end of the arms of the clamp so that a tool can be used by the surgeon to securely grasp the clamp during placement thereof on the vasculature or other tissue of the patient. The fixture can have a plurality of channels so that the user can select the angular orientation of the tool relative to the damp.

20 Claims, 12 Drawing Sheets

TISSUE CLAMP

CROSS REFERENCE TO RELATED APPLICATIONS

This application claims the priority of U.S. Provisional Application No. 60/732,748 filed Nov. 2, 2005, and co-pending U.S. patent application Ser. No. 11/592,019 filed Nov. 2, 2006, entitled "Tissue Clamp, the entire contents of the above applications being incorporated by reference herein.

BACKGROUND OF THE INVENTION

In vascular surgical procedures, the surgeon needs to control the vessel undergoing treatment, repair, or reconstruction. The vessel typically needs to be dissected and isolated to provide for the requisite controlled manipulation. Once isolated, the vessel needs to be clamped to stop blood flow while performing a bypass or other surgical manipulation of the artery or vein. Clamps can also be used to temporarily or permanently prevent the flow of blood into a vascular aneurysm or to align tissue such as nerve endings or the urethra.

The clamp is generally held by forceps and handed to the surgeon for placement. The surgeon then manipulates the clamp to achieve the correct orientation for proper placement on the vessel. Existing clamps and the forceps used to hold them make it difficult to securely hold the clamps, which may slip out of the forceps during use. Existing clamps typically have two arms that are connected to a spring-loaded hub. The proximal ends are manually compressed together to open the distal ends.

However, due to the limited ability of current forceps to manipulate and stably apply clamps, there is an ongoing need for improvements in vascular clamp operation to improve safety and ease of use.

SUMMARY OF THE INVENTION

The system and method of the present invention includes a tissue clamp having a fixture or peg that protrudes from the proximal end of the clamp. This feature provides for the clamp to be grasped and securely placed about tissue such as an artery. A preferred embodiment of the invention utilizes a tool that engages the fixture to prevent premature release of the clamps during placement. An example of a tool is a pair of forceps having an opening or eyelet at the distal end that is shaped to securely engage the fixture on the clamp. The tool and fixture can be configured to allow the user to rotate the clamp in the tool and thereby select the rotational orientation of the clamp to the tool.

A preferred embodiment of the invention has a tool and clamp system in which the tool can be rotated in at least two different directions relative to the clamp. Preferably the tool can be rotated both vertically and horizontally relative to the clamp axis so that the user can place the clamp easily in the proper location at the surgical site without having to disturb additional tissue or other surgical instruments, and with minimal effort by the user.

A preferred embodiment of the invention utilizes a fixture that has one or more channels or grooves that allow the tool to more securely engage the clamp fixture. This can also provide a particular orientation of the tool relative to the clamp. The opening or eyelet of the tool can be provided with members such as ridges or teeth that are sized to mate with the channels or grooves on the clamp fixture. A surgeon can select a particular orientation of the tool to the clamp and thereby provide a preferred orientation of the clamp to grasp the vessel. The surgeon can also rapidly realign or adjust the angular orientation during placement.

In another preferred embodiment, the opening on the tool that receives the fixture can be larger and of a different shape than the fixture so as to allow the user to grasp the clamp with the tool at different positions and/or orientations. Alternatively, the fixture can be circular, oval or a simple peg with a smooth cylindrical or cone shape extending from a surface of the clamp arm that mates exactly the shape of the opening in the forceps. The opening on the forceps can extend along an axis that is at an oblique angle relative to the longitudinal axis of the forceps arm to provide a further range of orientation options during placement. The forceps or other type of grasping clamp can be provided with a threaded screw locking device or ribbed jaws extending from the forceps arms that engage and lock such that when the user presses the arms or handles of the tool together that grasp the clamp in a locked position. This allows the tool and clamp to be passed from one person to another without risk of releasing the clamp inadvertently before proper placement.

In another embodiment a reverse hinge and clip lock forceps can be used to grasp the clamp. In this embodiment the resting state of the forceps is closed. Thus, the hinge is pushed to open the forceps and enable the user to pick up the clamp. By releasing the pressure exerted to open the forceps, the distal arms or jaws of the forceps engage the fixture on the clamp.

The clamps can be provided in various sizes and shapes to accommodate use thereof for various applications including vascular procedures such as cardiovascular and microvascular surgery, nerve approximation surgery or urethral repair. The clamps and tools of the present invention can be made using metal and/or plastic components. The foregoing and other features and advantages of the system and method for using vascular clamps will be apparent from the following more particular description of preferred embodiments of the system and method as illustrated in the accompanying drawings in which like reference characters refer to the same parts throughout the different views.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Illustrated in FIGS. 1-4 is a vascular clamp 10 having a fixture 20 on an arm 12 of the clamp that allows the clamp to be grasped by a tool that can be used by a surgeon, for example, to securely grasp and place the clamp during a surgical procedure. A preferred embodiment uses a second fixture 22 on the second arm 14 of the clamp so that a tool can securely grasp both arms.

The clamp is preferably used with a tool having elements that grasp fixtures 20, 22 and press the proximal ends of arms 12, 14 together to open the distal ends 18. The clamp is then positioned in proximity to a surgical site such that the open distal ends of arms 12, 14 can be positioned on opposite sides of an artery to be clamped. The surgeon then releases pressure exerted by the tool on the proximal ends of the arms of the clamp thereby allowing the distal ends to grasp and occlude the artery. This prevents blood flow to the surgical site such as a location for a graft, which can then be sutured onto the artery without loss of blood or visual obstruction of the procedure.

A preferred embodiment of the invention utilizes a fixture 20 having features on its surface that mate with features of the tool used to grasp the clamp. These features can be seen in the enlarged perspective view of the fixture 20 shown in FIG. 2. The fixture 20 has a top 28, a sidewall 24, a plurality of channels or grooves 26 and a base 25. The sidewall slopes at an angle between 60 and 80 degrees with an increasing diameter toward the base.

Another preferred embodiment of the fixture can include an aperture or opening in one or both arms that can also be engaged by forceps or tool that grasps one or both arms of the clamp. The distal end of the tool can have features that mate with channels or features associated with the aperture, opening or other feature of the clamp to provide a fixed orientation between he tool and the clamp.

Figures 1, 2:
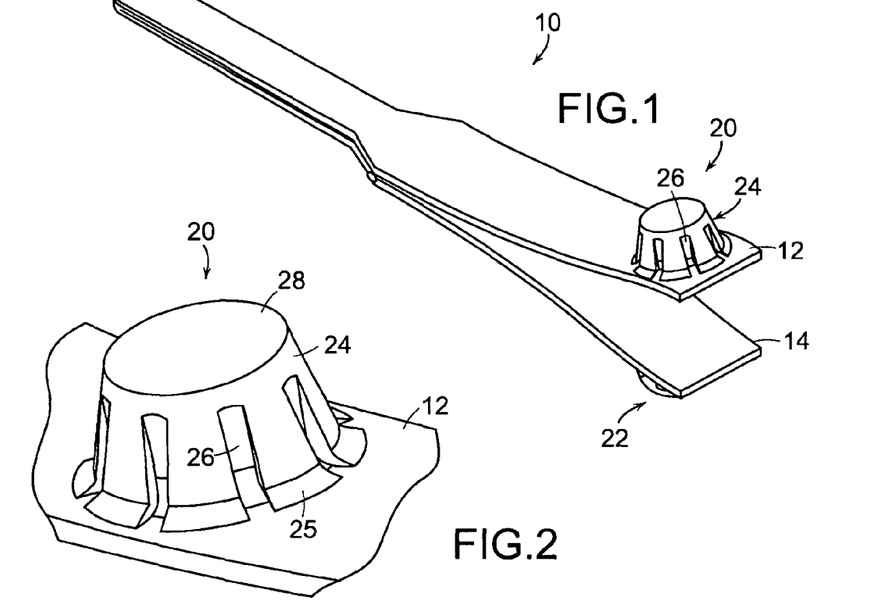
FIG. 1 is a perspective view of clamp in accordance with the invention.
FIG. 2 is an enlarged perspective view of a surgical clamp fixture in accordance with the invention.
Figure 3:
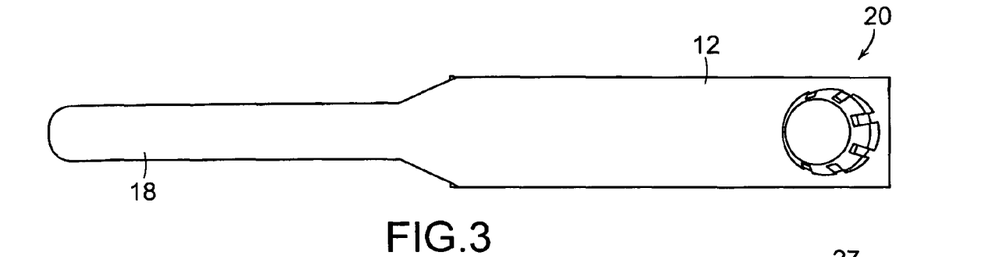
FIG. 3 is a top view of a clamp arm with a fixture thereon in accordance with the invention.
Figure 4:
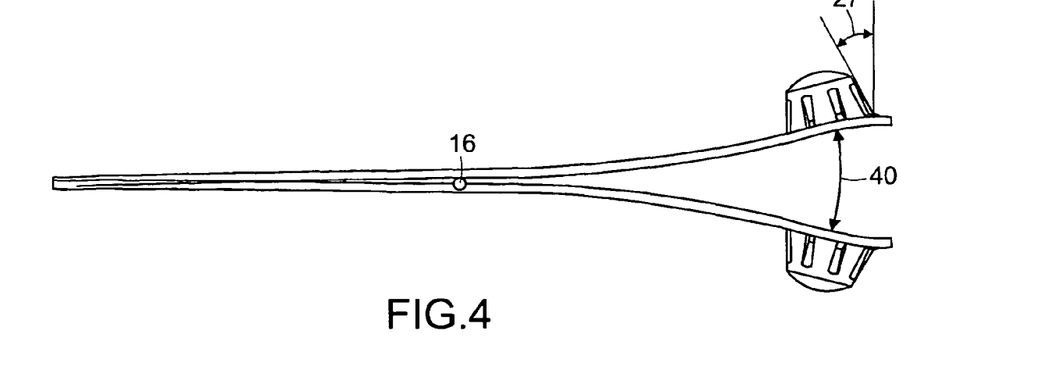
FIG. 4 is a side view of a surgical clamp in accordance with the invention.
Figure 5:
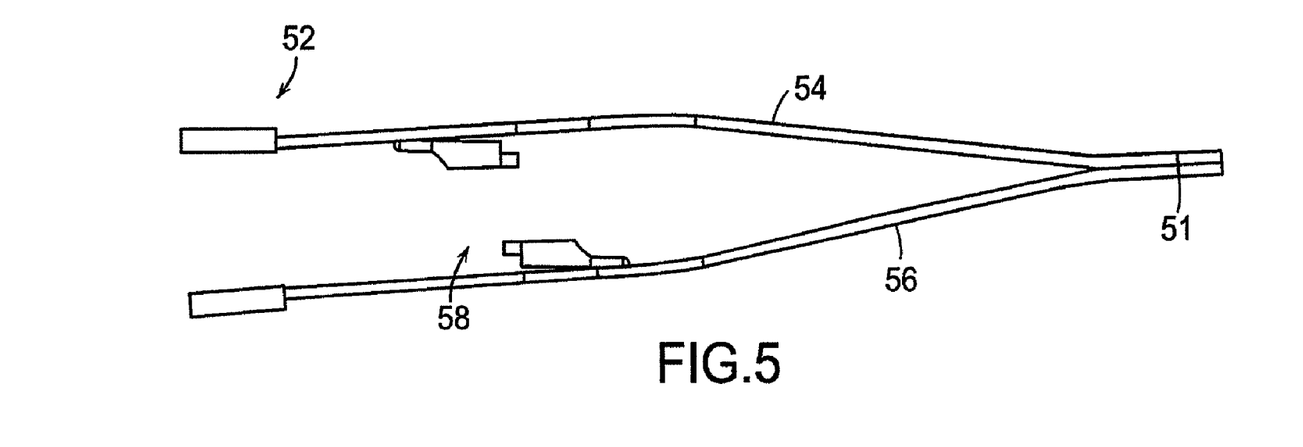
FIG. 5 is a top view of a forceps in accordance with the invention.

The top view of FIG. 3 shows a generally circular shape of the fixture 20. The side view of the clamp 10 shown in FIG. 4 shows the distance 40 that the user can squeeze the arms together. The sidewall 24 can slope at angle 27 as described above.

Illustrated in FIGS. 5-8 is a clamping forceps tool 50 that can be used to grasp the vascular clamp 10. The forceps 50 uses a connecting element 52 that engages the fixture 20 on the clamp. The forceps 50 has arms 54, 56 which are secured at one end 51 and are biased in an open position at the distal end so that they will easily fit around the clamp fixtures 20, 22 in the open positions. The arms 54, 56 can then be pressed together causing the distal ends of the clamp to open.

A locking element 58 can be used to secure the arms 54, 56 in a fixed position relative to each other. This allows the user to grasp the damp with the forceps and lock the clamp in an open position until the clamp is positioned properly to grasp the artery or nerve of the patient, for example.

Figure 6:
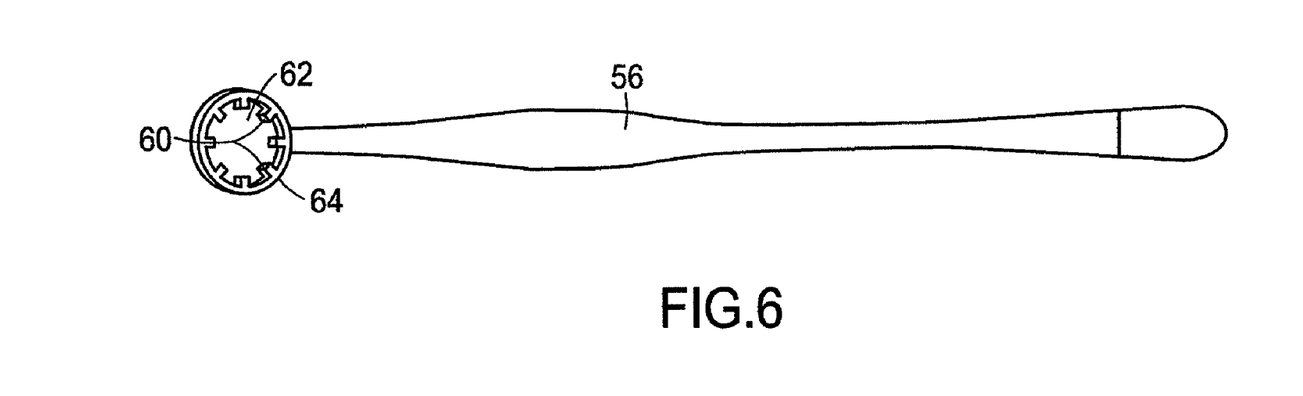
FIG. 6 is a top view of a forceps for grasping a clamp in accordance with the invention.

As shown in FIG. 6, the connecting element in a preferred embodiment includes a circular eyelet 64 having an opening 62 that mates with an upper or lower fixture of the clamp 10. The inner wall can have ridges 60 that correspond to channels 26 in the sidewall of the fixture. In this particular embodiment, eight ridges are shown; however, one or more ridges can be used.

Figures 7, 8:
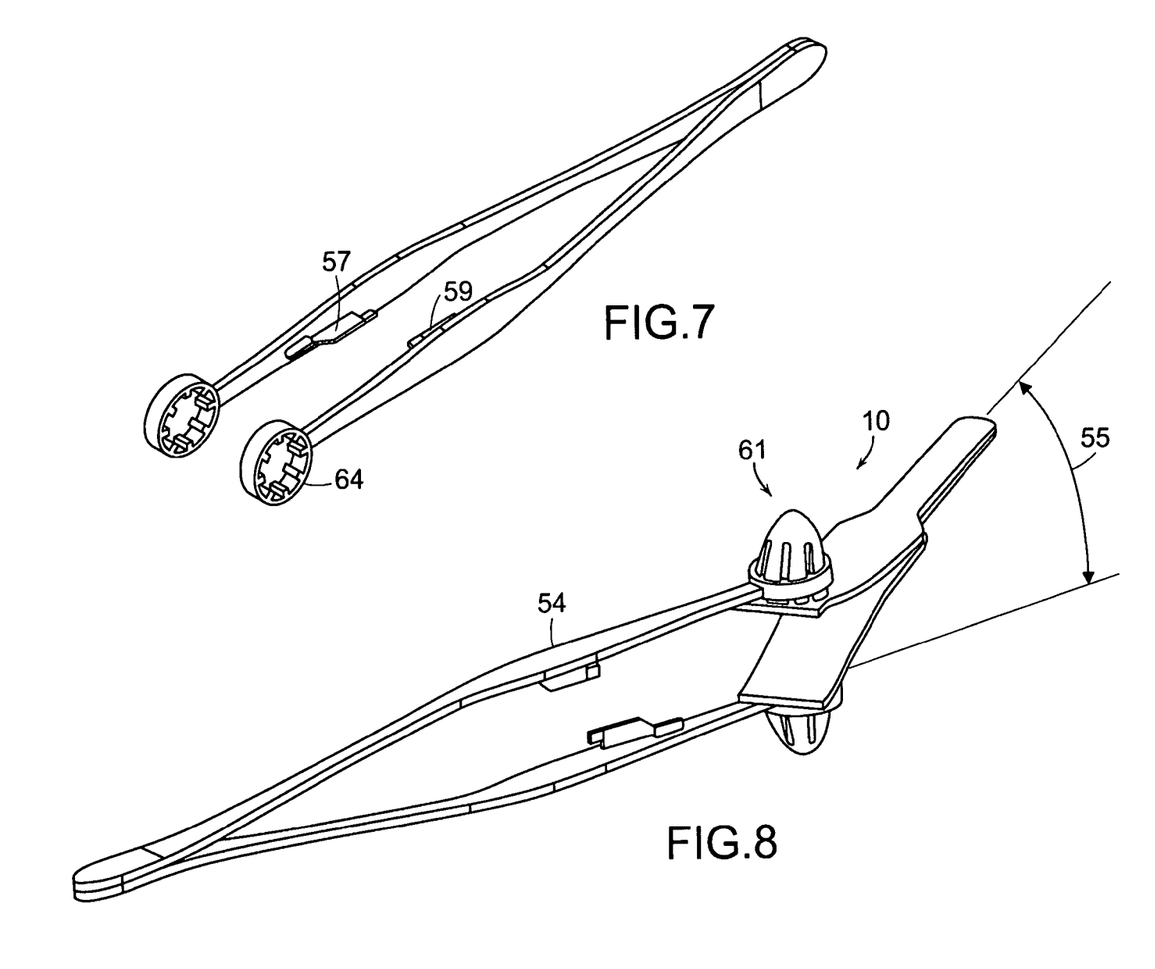
FIG. 7 is a perspective view of a forceps in accordance with a preferred embodiment of the invention.
FIG. 8 is a rear perspective view of a forceps for grasping a vascular clamp in accordance with the invention.

A perspective view of the forceps 50 is shown in FIG. 7. The forceps 50 can be aligned with the longitudinal axis of the clamp for placement. The locking element 58 can include a coupling or locking member 57,59 on each arm. Alternatively, the tool 50 can be positioned off-axis with the clamp 10 at oblique angle 55 as shown generally in FIG. 8. Thus, the orientation of the tool to the clamp can be selected to provide for ease of access to the surgical site. The ridges allow the orientation of the clamp relative to the grasping tool to be selected by the user. As illustrated the number of ridges is eight, however, other embodiments can incorporate more ridges using a saw tooth design having up to one hundred or more teeth thus allowing a greater number of angles that can be selected by the user. As illustrated in FIG. 8, the height of the fixture 61 is greater than the width of the tool extending over the fixture. As illustrated in FIGS. 1-4, the fixture can have a lower profile having a height that matches the width of the tool eyelet thus making it easier for the user to turn the tool to a different angle relative to the clamp.

Figure 9:
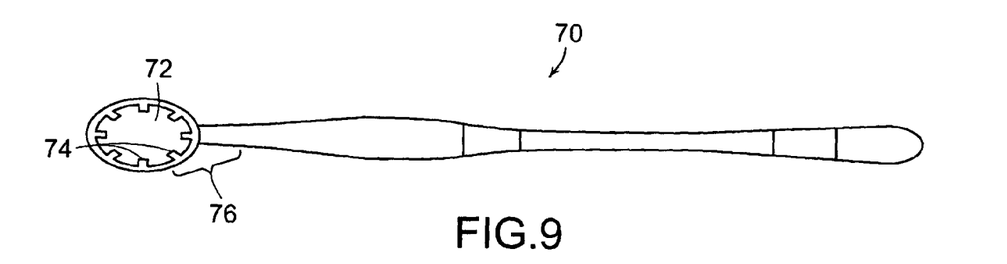
FIG. 9 is a side view of another preferred embodiment of a forceps used in accordance with a preferred embodiment of the invention.
Figure 10:
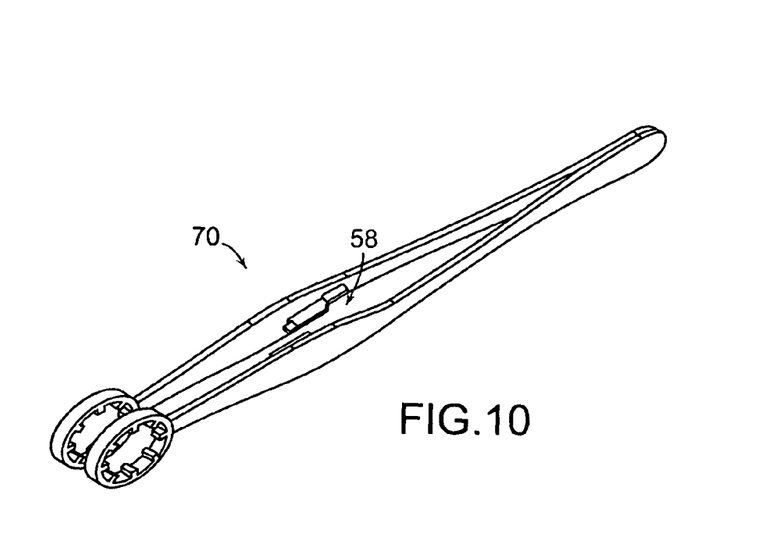
FIG. 10 is a perspective view of the embodiment shown in FIG. 9.

Another preferred embodiment is shown in FIGS. 9 and 10 in which a forceps 70 has an oval shaped opening 72 with ridges 74 to engage the fixture. The angle 76 between the forceps arm and the connecting placement can be manufactured at different oblique angles to provide different orientations. A threaded locking device can be used or a pair of ribbed jaws extending toward each other from the arms of the forceps can be pressed together and thereby lock the arms in a fixed position. Note that a scissor-type of forceps with grasping jaws extending from a hinge can also be used.

In another embodiment a reverse hinge forceps can also be used to grasp the clamp. Instead of being manufactured to be at rest in the open position, the forceps can be formed as a spring at rest in the closed position. In this embodiment, the user presses the arms together to open the forceps to enable the user to grasp the fixture on the vascular clamp. The user then relaxes their grip such that the distal opening on the forceps securely grasps the fixture in a rest position.

Figure 11:
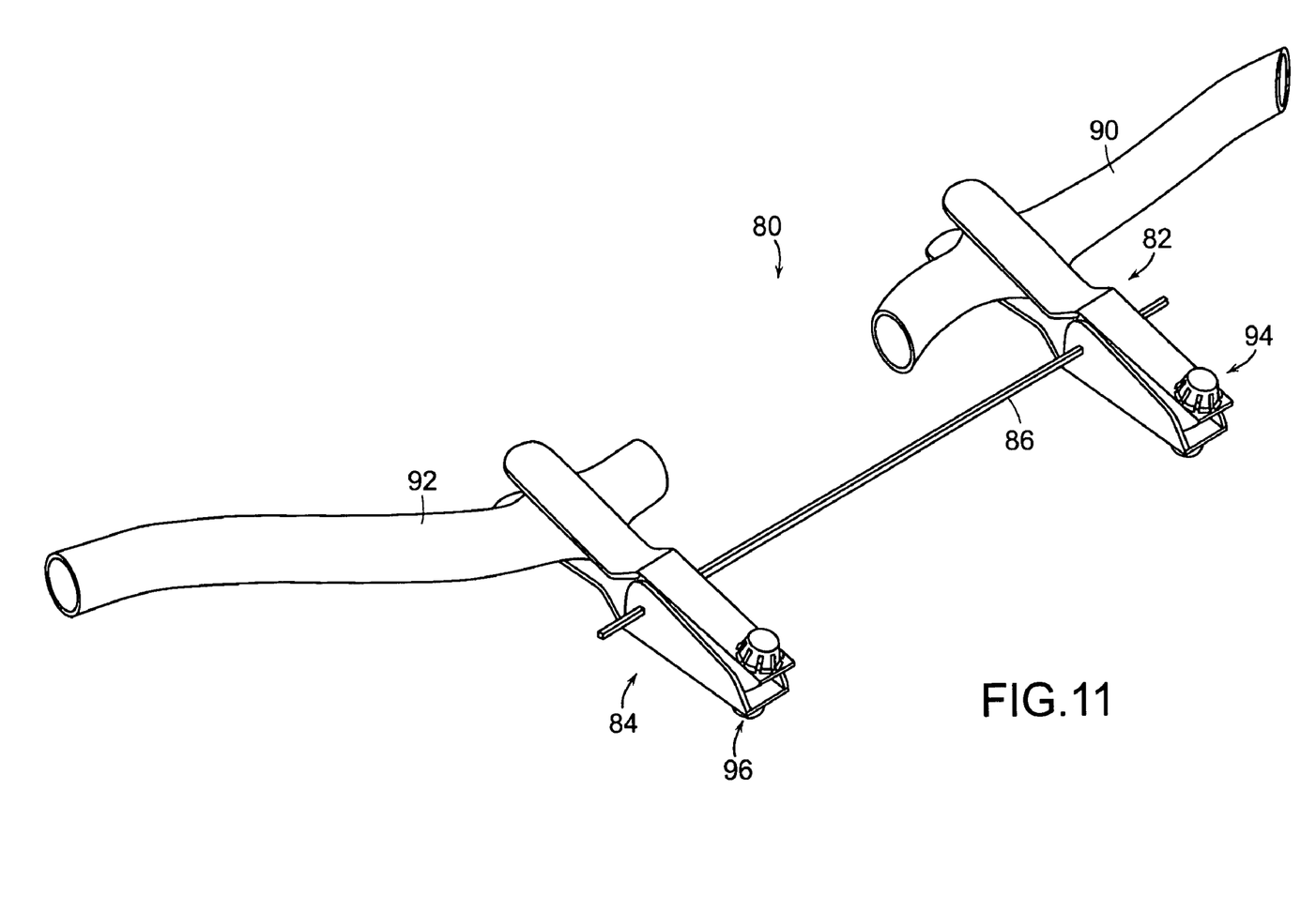
FIG. 11 illustrates another preferred embodiment of the invention including a pair of aligned clamps.

Shown in FIG. 11 is a preferred embodiment in which a plurality of clamps are connected together to provide a clamp device 80 that can be used to position tissue such as nerve sections or vascular sections 90, 92 which can be aligned with respect to one another to enable surgical repair. The device 80 can be used with other body lumens such as the urethra or other tubular structures such as those in the gastrointestinal system. In this particular embodiment, a pair of clamps 82, 84 are connected by a bar 86 or other connector. The arms of the clamps 82, 84 each have fixtures 94, 96 to grasp the clamp with a tool as described previously herein.

Figure 12:
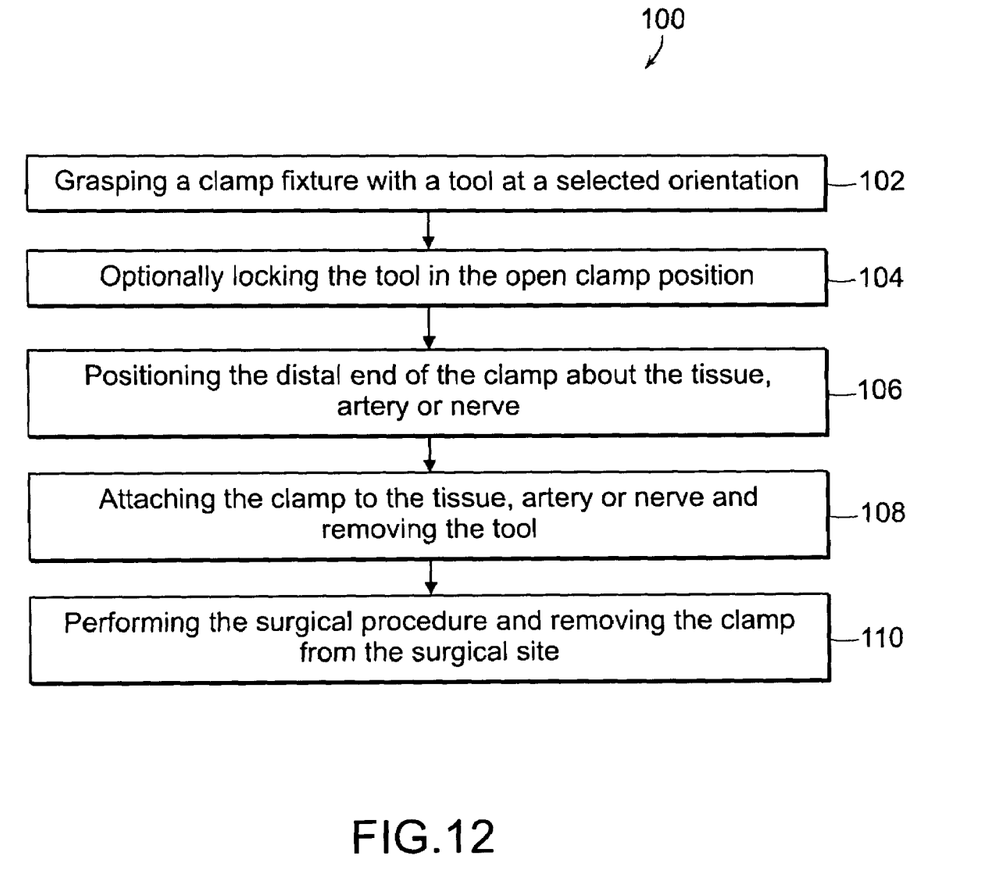
FIG. 12 illustrates a method of performing a procedure in accordance with a preferred embodiment of the invention.

A method 100 of using a clamp device for a surgical procedure is illustrated in FIG. 12. First, the clamp fixture is grasped 102 with a tool at a selected orientation. The clamp can be optionally locked 104 in the open position during placement. The surgeon or other user then positions 106 the open distal ends of the clamp about the tissue such as an artery or nerve. The clamp is attached 108 to the tissue and the tool removed. The procedure 110 is then performed and the clamp removed, if necessary.

Figure 13A:
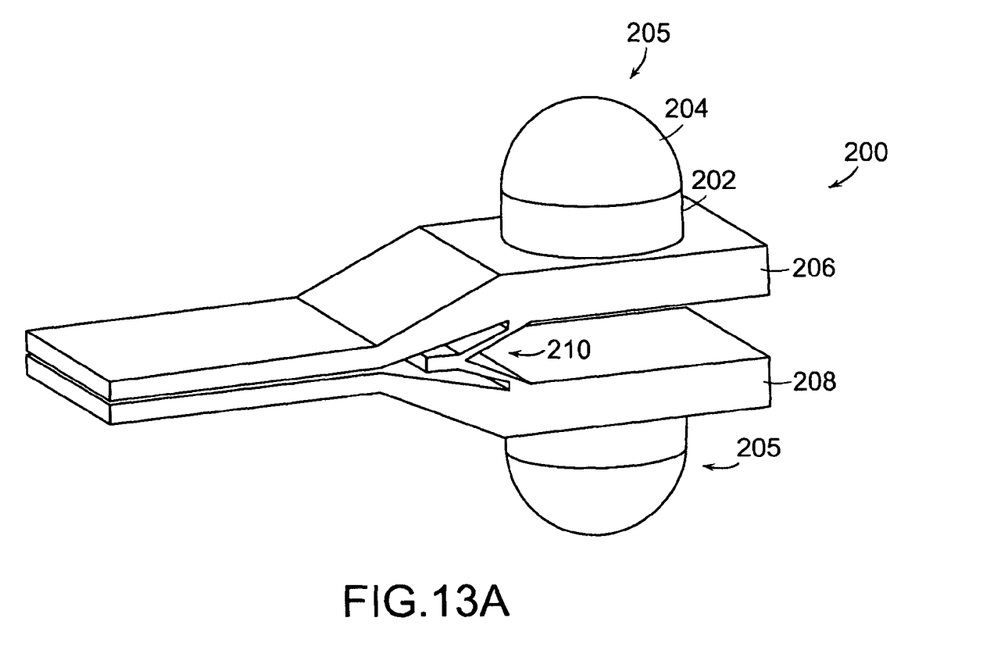
FIGS. 13A and 13B illustrate another preferred embodiment of a clamp in accordance with the invention.
Figure 13B:
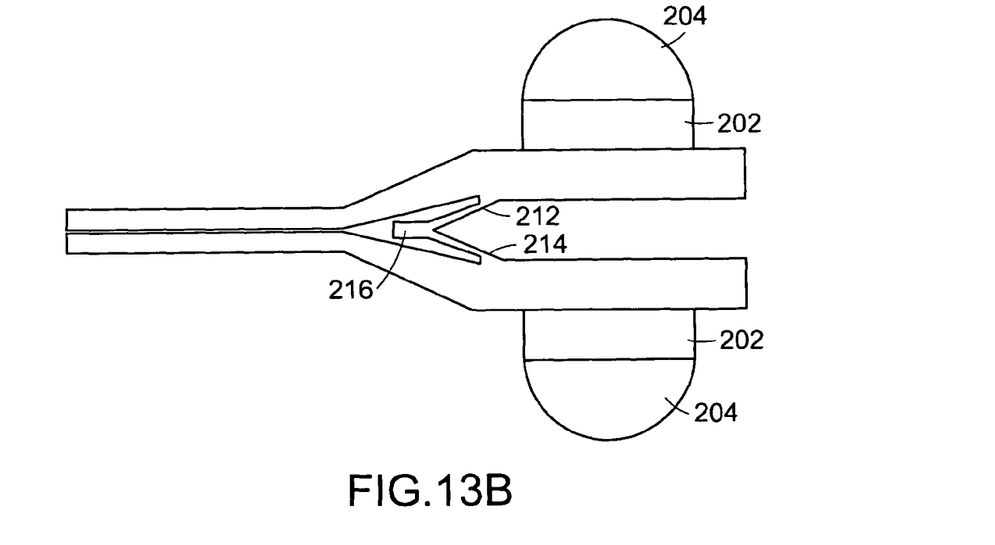

FIGS. 13A and 13B illustrated a perspective and side views of another preferred embodiment of a clamp in which each fixture 205 comprises a cylindrical base 202 and a hemisphere or dome shaped portion 204. Each arm 206, 208 has a proximal end which can be moved towards each other. The arms can be connected by a joint 210 that can include a first joint arm 212 and a second joint arm 214 that are attached to joint element 216.

Figures 14A, 14B, 14C:
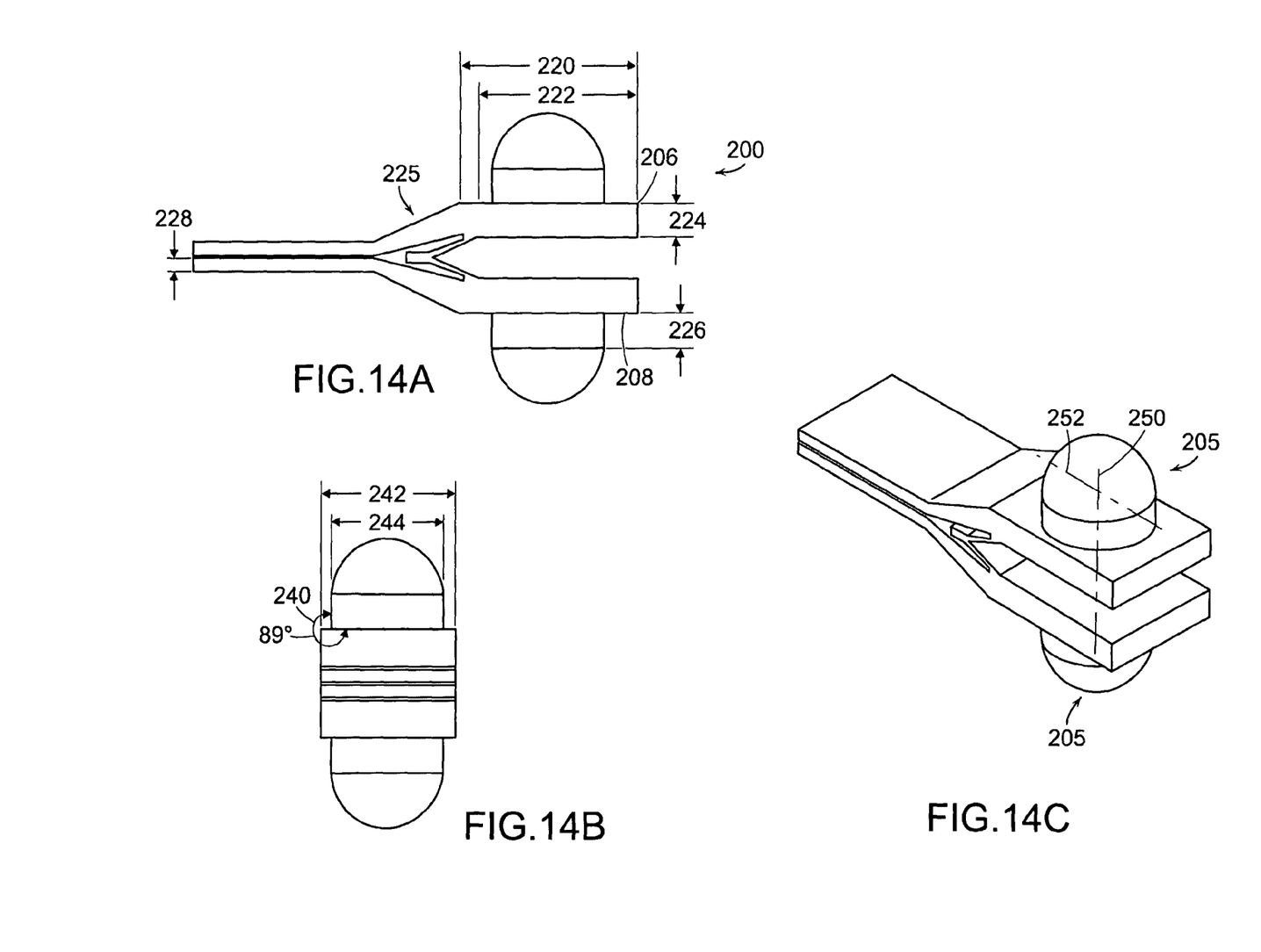
FIGS. 14A-14C illustrate side, end and perspective views of a sample clamp.

FIG. 14A shows a preferred embodiment in which each arm 206, 208 has a proximal thickness 224, which can be about 0.8 mm and a thinner distal end thickness 228, which can be about 0.3 mm. The length 222 of distal end of the arm 206, 208 up to the joint can be about 3.6 mm and the length 220 of each arm to the shaped section 225 of each arm can be about 4 mm. The cylindrical portion of each fixture 202 can have a height 226 (FIG. 14B) that can be about 0.8 mm, a upper diameter 244 of about 2.5 mm with the outer wall shaped at an angle of less than 90°, preferably about 89°. The width 242 of the arm can be about 3 mm. The dimensions of the clamp can be increased or decreased depending upon the particular application and clamping pressure needed for that application. The fixture 205 is aligned along a common rotational axis 250 about which the tool grasping the clamp can rotate, and are also situated along a longitudinal plane 252 (FIG. 14C).

Figure 15A:
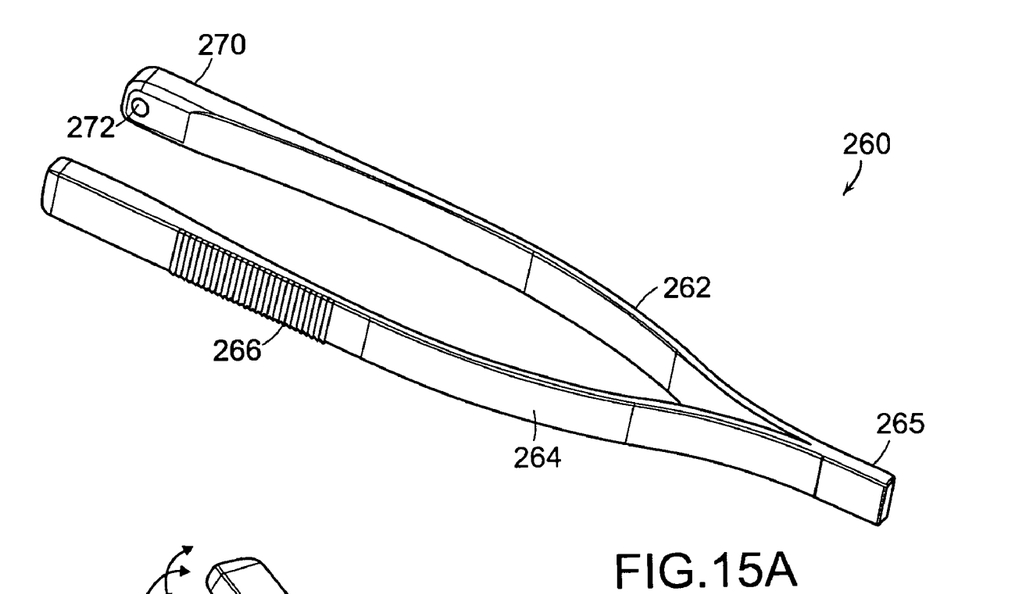
FIGS. 15A and 15B are perspective views of a tool for grasping clamp in accordance with a preferred embodiment of the invention.
Figure 15B:
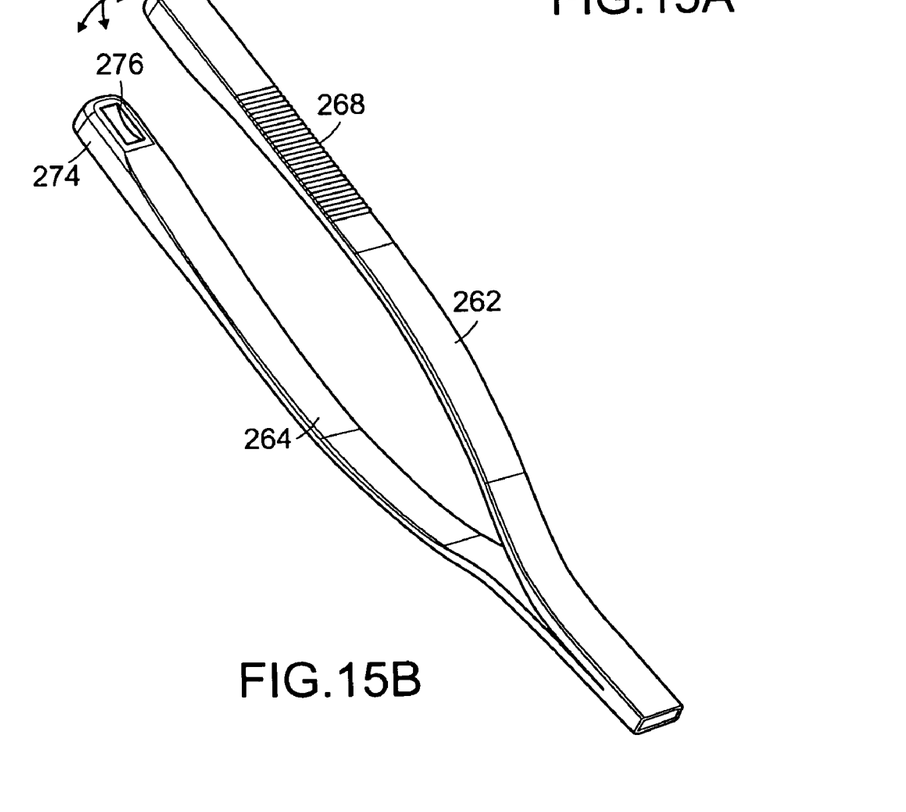

FIGS. 15A and 15B illustrate differing perspective views of a tool 260 for grasping the clamps in accordance with a preferred embodiment of the invention. The tool 260 includes a first arm 262, a second arm 264 connected at joint 265. First arm 262 has a roughened or ridged surface 268 that can be frictionally engaged with the fingers of a user and distal end 270 with a first interface element 272 that receives a first fixture element 205 and can be shaped to be hemispherical, or any other shape that matches the fixture element shape. The second arm 264 can be identical to the first arm having a frictional surface 266 and a distal end with a second interface element 276 that can be the same as element 272, except facing in the opposite direction, or alternatively, interface element 276 comprises a groove or channel in which the fixture 205 can slide longitudinally so that the tool can be rotated in a second direction relative to the clamp 200. Thus, in this embodiment, the tool can be moved relative to the clamp along two different rotational axes. The interface and/or channel can also have surface features such as dimples or grooves that match surface features of the one or more fixture elements to provide a more secure connection between the tool and the clamp.

FIGS. 16A-16G illustrate detailed dimensional features of a preferred embodiment of the invention that can be varied for the specific application depending on the size needed and the clamping force required. The outer diameter 280 of the arms 262, 264 (section AA shown in FIG. 16A) can be 30 mm, for example, with the inner spacing 282 being sized to extend over opposite sides of the two clamp fixtures 205, for example, 20 mm.

Figure 16A:
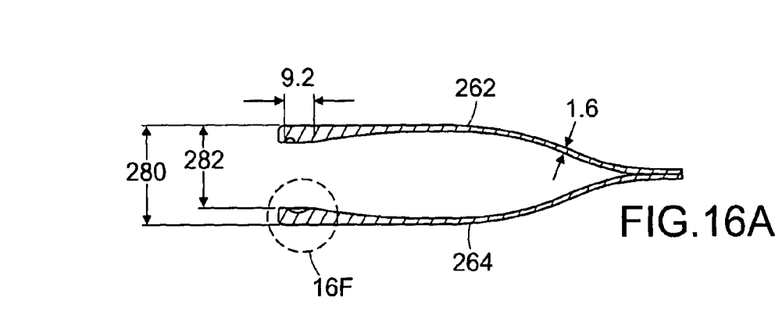
FIGS. 16A-16G illustrate sectional views of a tool in accordance with an embodiment of the invention.
Figure 16B:
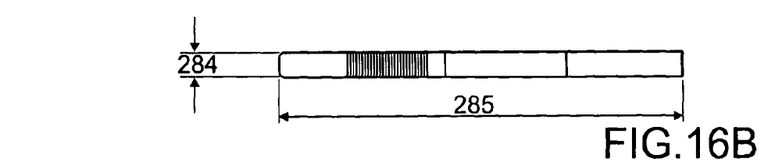
Figure 16C:
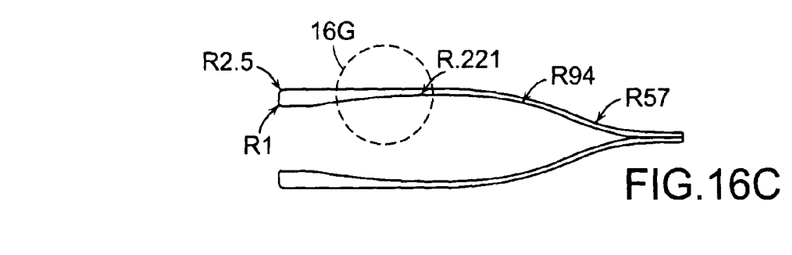
Figure 16D:
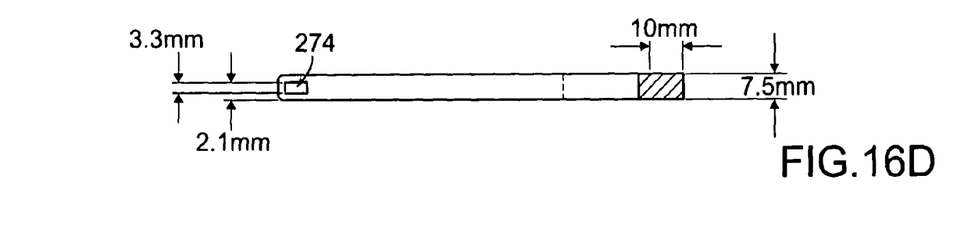
Figure 16E:
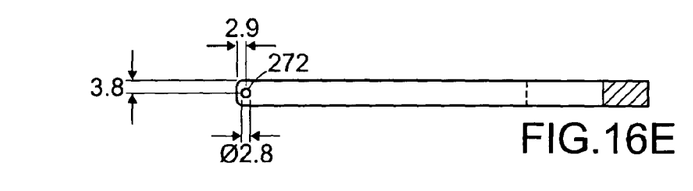
Figure 16F:
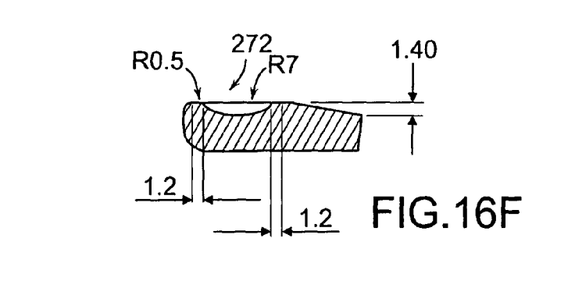
Figure 16G:
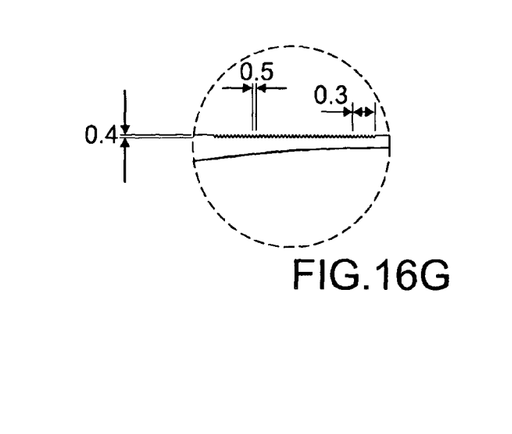
Figure 17:
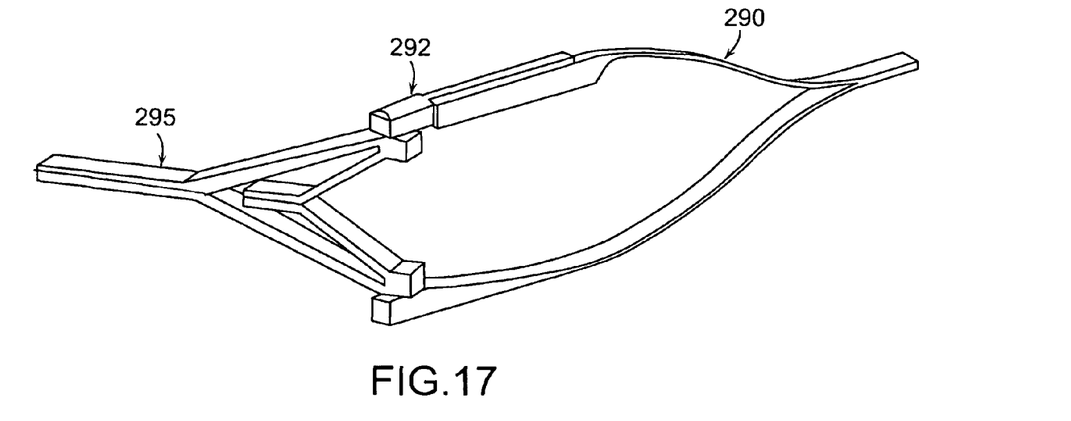
FIG. 17 illustrates a tool grasping a clamp at an oblique angle.
Figure 18:
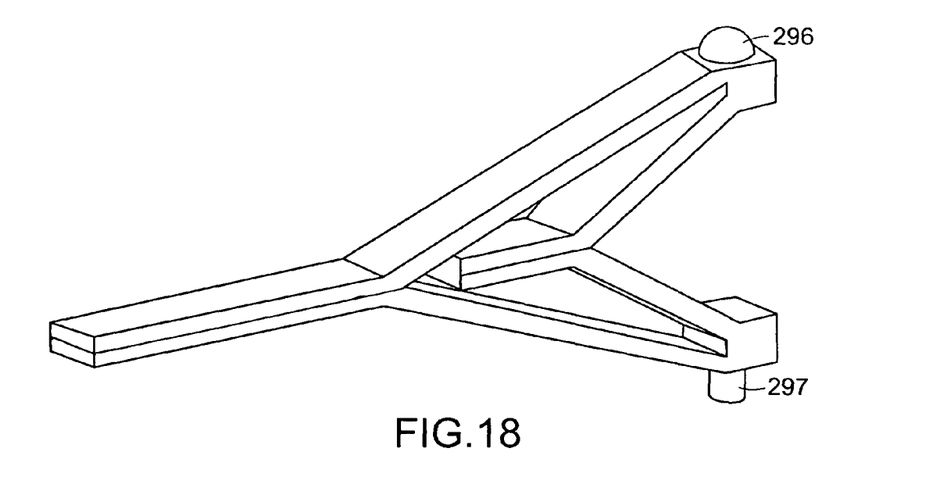
FIG. 18 illustrates a perspective view of a clamp.
Figure 19:
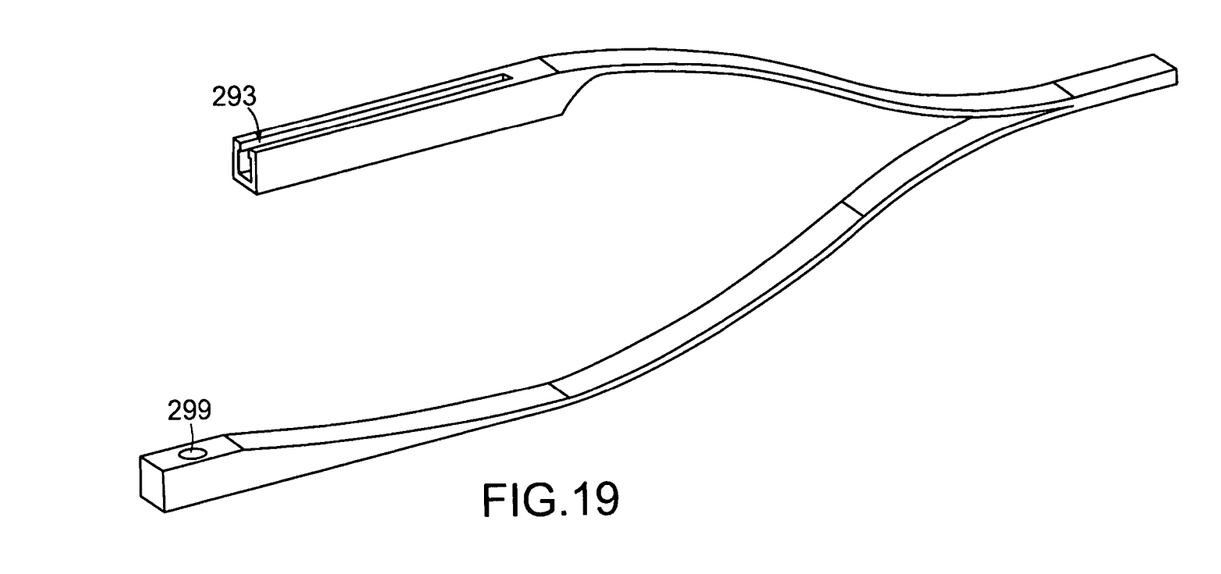
FIG. 19 illustrates a first element of a clamp having separate sections.
Figure 20:
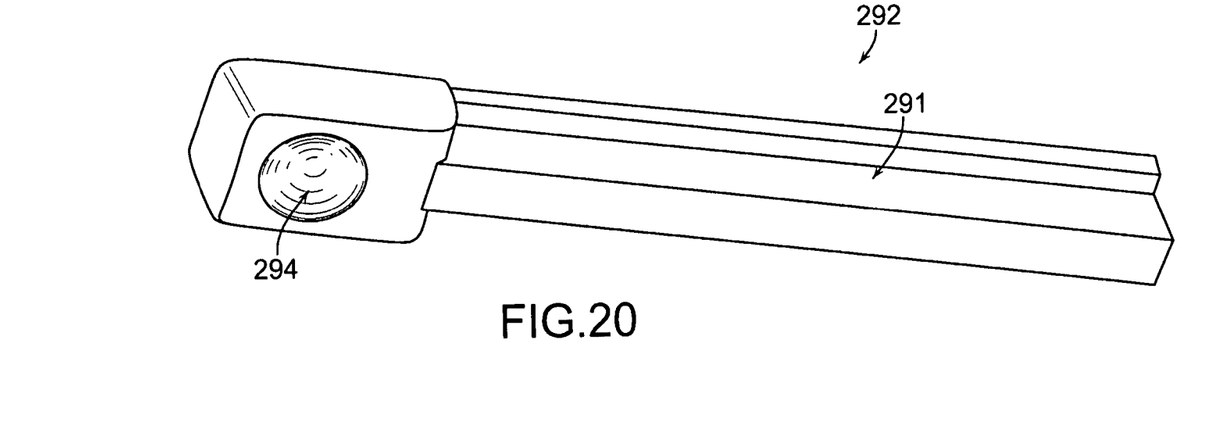
FIG. 20 illustrates a second section of a tool that mounts onto an arm of the tool element of FIG. 19.

The width of each tool arm 284 can be 7.5 mm and the length 285 can be about 125 mm. the features shown in FIG. 16C can have the indicated radii for this preferred example. Section 13B shown in FIG. 16D can have a channel with the width and length shown. Section DD shown in FIG. 16E can have the hemispherical element 272 with dimensions shown in this preferred example. Feature C and E for this example are illustrated in FIGS. 16F and 16G, respectively.

FIGS. 17-20 illustrate another preferred embodiment in which tool 290 has a section 292 that has a slide 291 that moves within channel 293 so as to alter the angle of elevation of the tool 290 relative to clamp 295. The fixtures 296, 297 are grasped with tool interface elements 294 and 299, respectively.

The claims should not be read as limited to the described order or elements unless stated to that effect. Therefore, all embodiments that come within the scope and spirit of the following claims and equivalents thereto are claimed as the invention.

What is claimed:

1. A tissue clamp system comprising:
a first arm and a second arm that are attached at a hub to provide a clamp such that the first arm and the second arm rotate relative to each other, the first arm and the second arm of the clamp each having a distal tip that adapted to grasp tissue of a patient, the clamp further having a fixture with a top and a raised sidewall on a proximal end of the first arm for grasping of the clamp by a user; and
a tool having an opening that receives the top of the fixture to grasp the clamp with the fixture such that the user can rotate the tool relative to the raised sidewall to grasp the clamp at each of a plurality of different angles.

2. The tissue clamp of claim 1 further comprising a second fixture with a raised sidewall on the second arm of the clamp.

3. The tissue clamp of claim 1 wherein the fixture further comprises a circular sidewall, and a base, the fixture being attached to the first arm at the base.

4. The tissue clamp of claim 1 wherein the sidewall further comprises a channel.

5. The tissue clamp of claim 1 wherein the sidewall comprises a plurality of vertically extending channels.

6. The tissue clamp of claim 1 wherein the tool can relax to grasp the clamp with the fixture in a first direction and a second direction.

7. The tissue clamp of claim 6 wherein the tool comprises a forceps.

8. The tissue clamp of claim 6 wherein the tool has a member that engages a feature on the fixture.

9. The tissue clamp of claim 1 wherein the sidewall of the fixture is shaped such that the tool can rotate relative to the clamp in a first direction about a fixture axis and rotate in a second direction to elevate the tool relative to the fixture axis to grasp the clamp in a plurality of angular positions.

10. The tissue clamp of claim 1 wherein the opening comprises an interface that mates with the fixture.

11. The tissue clamp of claim 1 wherein the fixture comprises a hemispherical shape.

12. A tissue clamp comprising:
a first arm and a second arm that are attached at a hub such that the first arm and the second arm rotate relative to each other, the first arm and the second arm each having a distal tip such that the clamp grasps tissue of a patient, and the clamp further comprising a first fixture on a proximal end of the first arm for grasping of the clamp by the user, the first fixture being attached at a first fixture base to the first arm and having a first fixture top and a first raised sidewall, the first raised sidewall having a sidewall diameter that is larger at the first fixture base than at the first fixture top and a second fixture on the second arm of the clamp, the second fixture being attached at a second fixture base to the second arm and having a second fixture top and a second raised sidewall.

13. The tissue clamp of claim 12 wherein the second fixture on the second arm of the clamp, extends from an opposite side of the clamp then the first fixture.

14. The tissue clamp of claim 12 wherein the first fixture first raised sidewall of the extends from the first fixture base to the first fixture top and the second raised sidewall of the second fixture extends from the second fixture base to the second fixture top.

15. The tissue clamp of claim 14 wherein the first raised sidewall comprises a channel.

16. The tissue clamp of claim 14 wherein the first raised sidewall comprises a plurality of vertically extending channels.

17. The tissue clamp of claim 12 further comprising a tool for grasping the clamp with the fixture.

18. The tissue clamp of claim 17 wherein the tool comprises a forceps.

19. The tissue clamp of claim 17 wherein the tool has a member that engages the first fixture such that the tool can be rotated about a first fixture axis in a first direction and rotated in a second direction to elevate the tool relative to the first fixture axis such that the tool can grasp the clamp at a plurality of angular positions.

20. The tissue clamp of claim 12 wherein the first fixture has a circular cross-section.

* * * * *